United States Patent
Desmond, III et al.

(10) Patent No.: US 6,264,624 B1
(45) Date of Patent: *Jul. 24, 2001

(54) DRAINAGE CATHETER DELIVERY SYSTEM

(75) Inventors: Joseph P. Desmond, III; Leslie P. Sherwood; D. H. Perkins, all of Bloomington, IN (US)

(73) Assignee: Boston Scientific Coporation, Natick, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/257,764

(22) Filed: Feb. 25, 1999

Related U.S. Application Data

(63) Continuation of application No. 08/911,323, filed on Aug. 14, 1997, now Pat. No. 5,921,952.

(51) Int. Cl.⁷ .................................................. A61M 5/00
(52) U.S. Cl. ................................................ 604/8; 604/523
(58) Field of Search ............................... 604/8, 264, 523, 604/164.01, 164.13, 165.01

(56) References Cited

U.S. PATENT DOCUMENTS

| | | |
|---|---|---|
| 2,212,334 | 8/1940 | Wallerich . |
| 3,332,424 | 7/1967 | Minteer ............................... 128/349 |
| 3,421,509 | 1/1969 | Fiore ................................... 128/349 |
| 3,592,197 | 7/1971 | Cohen ................................. 128/349 |
| 3,783,453 | 1/1974 | Bolie ........................................ 3/1 |
| 3,908,635 | 9/1975 | Viek ................................. 128/2 M |
| 3,938,529 | 2/1976 | Gibbons .......................... 128/349 R |
| 3,995,642 | 12/1976 | Adair ............................... 128/349 R |
| 4,225,979 | 10/1980 | Rey et al. ................................... 3/1 |
| 4,242,304 | 12/1980 | Ryder ................................... 422/119 |
| 4,248,214 | 2/1981 | Hannah et al. ......................... 128/7 |
| 4,307,723 | 12/1981 | Finney ............................. 128/349 R |
| 4,334,327 | 6/1982 | Lyman et al. ............................. 3/1 |
| 4,382,445 | 5/1983 | Sommers ................................. 604/8 |
| 4,434,797 | 3/1984 | Silander .............................. 128/343 |
| 4,474,569 | 10/1984 | Newkirk .................................. 604/8 |
| 4,484,585 | 11/1984 | Baier .................................... 128/748 |
| 4,500,313 | 2/1985 | Young .................................. 604/280 |
| 4,531,933 | 7/1985 | Norton et al. ........................... 604/8 |
| 4,568,338 | 2/1986 | Todd ................................... 604/281 |
| 4,592,341 | 6/1986 | Omagari et al. ........................ 128/4 |
| 4,610,657 | 9/1986 | Densow ................................... 604/8 |
| 4,643,716 | 2/1987 | Drach ..................................... 604/8 |
| 4,645,493 | 2/1987 | Ferrando et al. .................... 604/174 |
| 4,671,795 | 6/1987 | Mulchin .............................. 604/281 |

(List continued on next page.)

*Primary Examiner*—Richard K. Seidel
*Assistant Examiner*—Cris Rodriguez
(74) *Attorney, Agent, or Firm*—Crompton, Seager & Tufte, LLC

(57) ABSTRACT

A drainage catheter delivery system for positioning a drainage catheter or stent within a body cavity, such as a ureter. The delivery system includes a guide catheter, a push catheter, a drainage catheter (or stent) and a retention device. The guide catheter includes an outer diameter sized to slidably receive the push catheter and the drainage catheter. In this regard, the push catheter is placed over the guide catheter proximal the drainage catheter. The retention device selectively connects the push catheter to the drainage catheter. During use, the delivery system is pre-assembled as described above. The assembled delivery system is directed within a body cavity such that a distal end of the guide catheter is in close proximity to the desired drainage catheter position. The push catheter is axially slid along the guide catheter to move the drainage catheter away from a proximal end of the guide catheter. Conversely, the drainage catheter is retracted, or moved toward the proximal end of the guide catheter by retraction of the push catheter. Retraction of the push catheter retracts the drainage catheter via the retention device. Once properly positioned, the drainage catheter is released from the retention device by retracting the guide catheter from the drainage catheter.

9 Claims, 4 Drawing Sheets

U.S. PATENT DOCUMENTS

| | | | |
|---|---|---|---|
| 4,684,369 | 8/1987 | Wildemeersch | 604/272 |
| 4,699,611 | 10/1987 | Bowden | 604/51 |
| 4,713,049 | 12/1987 | Carter | 604/8 |
| 4,738,667 | 4/1988 | Galloway | 604/281 |
| 4,747,833 | 5/1988 | Kousai et al. | 604/164 |
| 4,755,175 | 7/1988 | Nilsson | 604/268 |
| 4,762,128 | 8/1988 | Rosenbluth | 604/96 |
| 4,783,454 | 11/1988 | Liu | 514/214 |
| 4,784,651 | 11/1988 | Hickey | 604/282 |
| 4,787,884 | 11/1988 | Goldberg | 604/8 |
| 4,790,809 | 12/1988 | Kuntz | 604/8 |
| 4,790,810 | 12/1988 | Pugh, Jr. et al. | 604/8 |
| 4,813,925 | 3/1989 | Anderson, Jr. et al. | 604/8 |
| 4,820,262 | 4/1989 | Finney | 604/8 |
| 4,822,333 | 4/1989 | Lavarenne | 600/30 |
| 4,824,435 | 4/1989 | Giesy et al. | 604/49 |
| 4,874,360 | 10/1989 | Goldberg et al. | 604/8 |
| 4,913,141 | 4/1990 | Hillstead | 606/108 |
| 4,913,683 | 4/1990 | Gregory | 604/8 |
| 4,931,037 | 6/1990 | Wetterman | 604/8 |
| 4,950,228 | 8/1990 | Knapp, Jr. et al. | 604/8 |
| 4,955,858 | 9/1990 | Drews | 604/8 |
| 4,957,479 | 9/1990 | Roemer | 604/8 |
| 4,963,129 | 10/1990 | Rusch | 604/8 |
| 4,973,301 | 11/1990 | Nissenkorn | 604/8 |
| 4,990,133 | 2/1991 | Solazzo | 604/8 |
| 4,994,066 | 2/1991 | Voss | 606/108 |
| 5,019,085 | 5/1991 | Hillstead | 606/108 |
| 5,019,102 | 5/1991 | Hoene | 623/12 |
| 5,052,998 | 10/1991 | Zimmon | 604/8 |
| 5,141,502 | 8/1992 | Macaluso, Jr. | 604/281 |
| 5,152,749 | 10/1992 | Giesy et al. | 604/164 |
| 5,282,784 | 2/1994 | Willard | 604/8 |
| 5,304,198 | 4/1994 | Samson | 604/194 |
| 5,320,604 | 6/1994 | Walker et al. | 604/96 |
| 5,322,501 | 6/1994 | Mahmud-Durrani | 604/8 |
| 5,324,259 | 6/1994 | Taylor et al. | 604/96 |
| 5,334,185 | 8/1994 | Giesy et al. | 604/164 |
| 5,348,537 | 9/1994 | Wiesner et al. | 604/96 |
| 5,364,354 | 11/1994 | Walker et al. | 604/96 |
| 5,372,600 | 12/1994 | Beyar et al. | 606/108 |
| 5,391,155 | 2/1995 | Sachse | 604/170 |
| 5,401,257 | 3/1995 | Chevalier, Jr. et al. | 604/265 |
| 5,405,378 | 4/1995 | Strecker | 623/1 |
| 5,407,435 | 4/1995 | Sachse | 604/170 |
| 5,454,788 | 10/1995 | Walker et al. | 604/96 |
| 5,458,615 | 10/1995 | Klemm et al. | 606/198 |
| 5,480,434 | 1/1996 | Eckstein et al. | 623/11 |
| 5,484,409 | 1/1996 | Atkinson et al. | 604/96 |
| 5,578,009 | 11/1996 | Kraus et al. | 604/96 |
| 5,599,291 | 2/1997 | Balbierz et al. | 604/8 |
| 5,645,533 | 7/1997 | Blaseser et al. | 604/164 |
| 5,653,748 | 8/1997 | Strecker | 623/1 |
| 5,669,880 | 9/1997 | Solar | 604/96 |
| 5,676,654 | 10/1997 | Ellis et al. | 604/103 |
| 5,681,274 | 10/1997 | Perkins et al. | 604/8 |
| 5,690,642 | 11/1997 | Osborne et al. | 606/108 |
| 5,693,015 | 12/1997 | Walker et al. | 604/96 |
| 5,776,099 | 7/1998 | Tremulis | 604/96 |

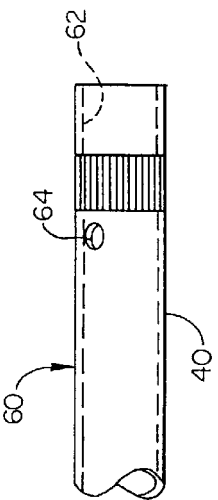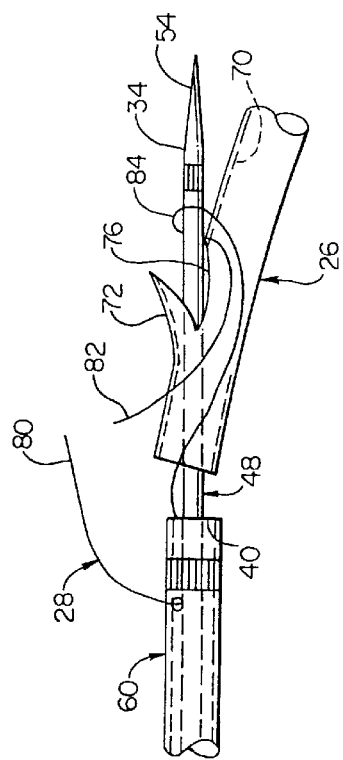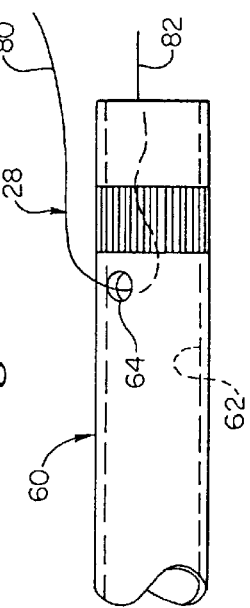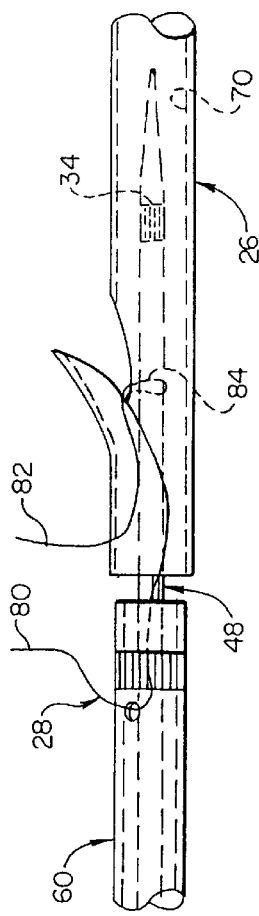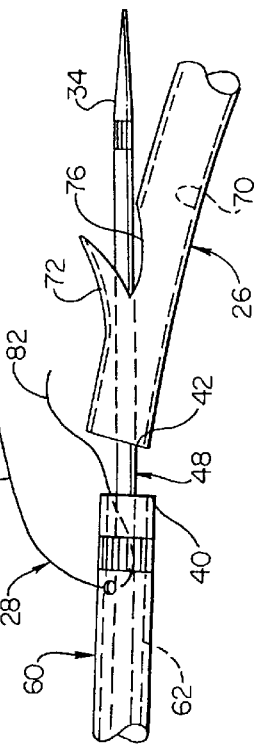

DRAINAGE CATHETER DELIVERY SYSTEM

This application is a continuation of application Ser. No. 08/911,323, filed Aug. 14, 1997, now U.S. Pat. No. 5,921,952.

BACKGROUND OF THE INVENTION

The present invention relates to a system for use in delivering a drainage catheter within a body cavity. More particularly, it is directed toward a preassembled device configured to provide single-step deployment and repositioning of a drainage catheter within the body cavity.

A drainage catheter or stent is widely recognized as an efficient and effective device for treating an obstructed body cavity, such as the ducts of the biliary tree or a ureter. These stents are used to bypass and drain an obstructed lumen and can be configured for long-term positioning within the lumen. It should be understood that the terms "drainage catheter" and "stent" can be used interchangeable with reference to these applications.

While drainage catheters are highly useful, proper placement of the drainage catheter often is a difficult and time-consuming procedure. Typically, an endoscope is first placed into the body cavity and positioned at the proper anatomical area. In this regard, a distal end of the endoscope is placed in close proximity to the desired area of drainage catheter placement. If necessary, a pre-dilating device is directed through the distal end of the endoscope to dilate the stricture. The dilating device is removed from the endoscope and replaced by a guide wire. Then, a guide catheter is placed over the guide wire and positioned near the stricture. The drainage catheter or stent is placed over the guide catheter until a proximal end of the drainage catheter is beyond a proximal end of the guide catheter. A push catheter is then placed over the guide catheter until a distal end of the push catheter abuts the proximal end of the drainage catheter. The drainage catheter is then pushed via the push catheter down the length of the guide catheter until the drainage catheter reaches the desired body cavity location. At this point, the drainage catheter is manipulated via the push catheter to secure the drainage catheter within the ureter.

Once properly positioned, the guide catheter and guide wire are removed from inside of the push catheter and the drainage catheter. The push catheter remains in place to prevent movement of the drainage catheter during removal of the guide catheter and guide wire.

Every effort is made to secure the drainage catheter at the proper location within the body cavity. However, there are times when the drainage catheter is placed too far into the body or migrates to a less desirable location in which case there are several time-consuming secondary procedures available. These may include placing the endoscope back into the body and directing a tool into the endoscope to grasp the drainage catheter and pull it back into position. It is impossible to retract the drainage catheter relative to the body cavity with the push catheter because there is only one point of interaction between the two components. Thus, retraction of the push catheter simply pulls the push catheter away from the drainage catheter. Positioning of the drainage catheter is unaffected by the push catheter retraction.

Drainage catheters or stents are highly useful devices. However, the procedures involved in positioning a drainage catheter or stent are highly time-consuming and leave little room for error. In fact, it is impossible to retract a drainage catheter with present push catheters without the use of additional tools. Therefore, a substantial need exists for a drainage catheter delivery system configured to allow one-step placement and simple repositioning of the drainage catheter.

SUMMARY OF THE INVENTION

The present invention provides a drainage catheter or stent delivery system for deploying a drainage catheter or stent within a body cavity. The delivery system includes a guide or guide catheter, a push catheter or placement catheter, a drainage catheter and a retention device. For purposes of this specification, it is understood that the term "drainage catheter" includes a stent.

The guide catheter is defined by a proximal end, an intermediate portion and a distal end. The push catheter includes a proximal end, a distal end and a central lumen running from the proximal end to the distal end. The central lumen of the push catheter is preferably sized to slidably engage an outer circumference of the guide catheter. Similarly, the drainage catheter includes a proximal end, a distal end and a central lumen sized to slidably engage an outer circumference of the guide catheter. Finally, the retention device is configured to selectively secure the drainage catheter to the push catheter. In one preferred embodiment, the retention device is a suture secured to the distal end of the push catheter.

The delivery system of the present invention is assembled by first sliding the push catheter over the intermediate portion of the guide catheter such that the proximal end of the push catheter is near the proximal end of the guide catheter. Similarly, the drainage catheter is slidably placed over the intermediate portion of the guide catheter, distal the previously-positioned push catheter. The retention device selectively secures the push catheter to the drainage catheter. In one preferred embodiment, the drainage catheter includes a passage from an outer circumference to the central lumen of the drainage catheter, defining a barb. The retention device, which preferably includes a suture extending from the distal end of the push catheter, is passed through the passage in the drainage catheter and around the guide catheter otherwise positioned within the central lumen of the drainage catheter.

During use, the delivery system of the present invention is pre-assembled as previously described. The delivery system is positioned with a body cavity such that the drainage catheter is proximate a desired location in the body cavity. The guide catheter is held stationary while the push catheter is slid over the guide catheter toward the distal end of the guide catheter. The distal end of the push catheter is sized to interact with the proximal end of the drainage catheter. Thus, distal movement of the push catheter imparts a distal movement onto the stent. Distal movement of the push catheter and reciprocal distal movement of the drainage catheter along the guide catheter is continued until the drainage catheter is positioned at the desired body cavity location.

Proximal movement or retraction of the drainage catheter is also available via movement of the push catheter. In this regard, the retention device transfers a retraction movement of the push catheter to the drainage catheter.

Once the drainage catheter is properly positioned within the body cavity, the drainage catheter is released from the guide catheter and push catheter. In one preferred embodiment, the push catheter is maintained in a stationary position while the guide catheter is retracted relative to the drainage catheter. As the distal end of the guide catheter nears the proximal end of the drainage catheter, the retention device is released from the drainage catheter.

In an alternative embodiment, the guide catheter includes a tapered tip at the distal end thereof. The guide catheter is configured such that upon final assembly, the tapered tip extends from the distal end of the drainage catheter. During use, the delivery system is directed into the body cavity such that the tapered tip of the guide catheter dilates a stricture in the body cavity.

BRIEF DESCRIPTION OF THE DRAWINGS

FIGS. 5–10 illustrate steps of assembling the delivery system in accordance with the present invention.

DETAILED DESCRIPTION OF THE INVENTION

Figure 1:
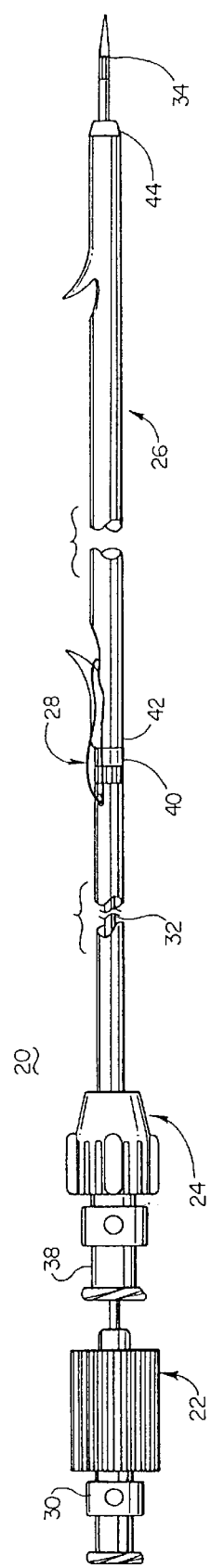
FIG. 1 is a side view of a delivery system in accordance with the prevent invention.

A preferred embodiment of a delivery system 20 is shown in FIG. 1. The delivery system 20 includes a guide catheter 22, a push catheter 24, a stent 26 and a retention device 28. Although described herein as a preferred device and method for delivering a stent or drainage catheter, the medical device deployment system could be utilized to deliver other units.

The various components of the delivery system 20 are described in greater detail below. Generally, however, the guide catheter 22 includes a proximal end 30, an intermediate portion 32 and a distal end 34. The push catheter 24 includes a proximal end 38 and a distal end 40. Similarly, the stent 26 includes a proximal end 42 and a distal end 44. The intermediate portion 32 of the guide catheter 22 is sized to slidably receive the push catheter 24 and the stent 26. Finally, the retention device 28 is configured to selectively secure the stent 26 to the push catheter 24. In this regard, the distal end 40 of the push catheter 24 is sized to abut the proximal end 42 of the stent 26. Thus, upon final assembly, distal movement of the push catheter 24 relative to the guide catheter 22 imparts a distal motion onto the stent 26 via interaction of the distal end 40 of the guide catheter 22 with the proximal end 42 of the stent 26. Conversely, proximal movement of the push catheter 24 relative to the guide catheter 22 imparts a similar proximal (or retraction) movement onto the stent 26 via the retention device 28.

Figure 2:
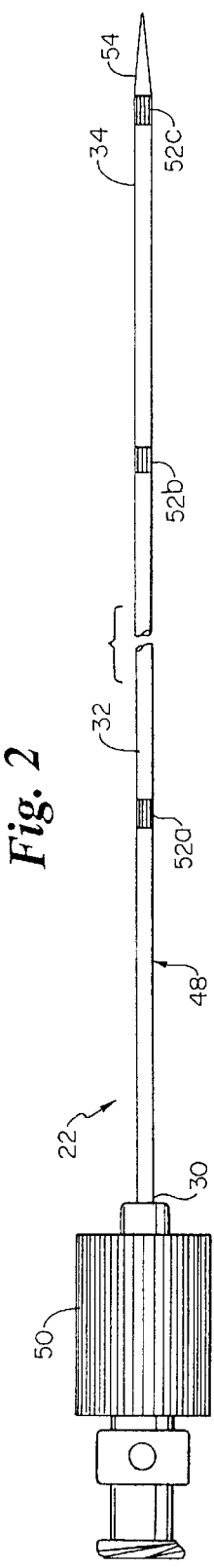
FIG. 2 is an enlarged side view of a guide catheter portion of the delivery system in accordance with the present invention.

The guide catheter 22 is shown in greater detail in FIG. 2. The guide catheter 22 includes a guide catheter body 48 defined by the proximal end 30, the intermediate portion 32 and the distal end 34, a male luer connector 50, radiopaque markings 52a–c and a central lumen (not shown). The male luer connector 50 is of a type commonly known in the art and is preferably positioned at the proximal end 30 of the guide catheter body 48. The radiopaque markings 52a–c are formed along the intermediate portion 32 at predetermined locations to assist in fluoroscopically determining system positioning.

The guide catheter 22 is preferably formed from a relatively stiff biocompatible polymer via an extrusion process. Alternatively, a biocompatible metal may be used. The central lumen (not shown) is preferably formed to extend from the proximal end 30 to the distal end 34. In the preferred embodiment, the central lumen is appropriately sized to slidably receive a guide wire and is preferably 0.038 inches in diameter. It should be recognized that other diameters are equally acceptable. With this configuration, the male luer connector includes a transverse passage (not shown) in communication with the central lumen for receiving a guide wire. Finally, the distal end 34 of the guide catheter body 48 is preferably formed to include a tapered tip 54. As described in greater detail below, the tapered tip 54 assists in dilation of a body cavity stricture. In a preferred embodiment, the tapered tip is coated with a lubricant to facilitate movement of the guide catheter body 48 within a body cavity.

Figure 3:
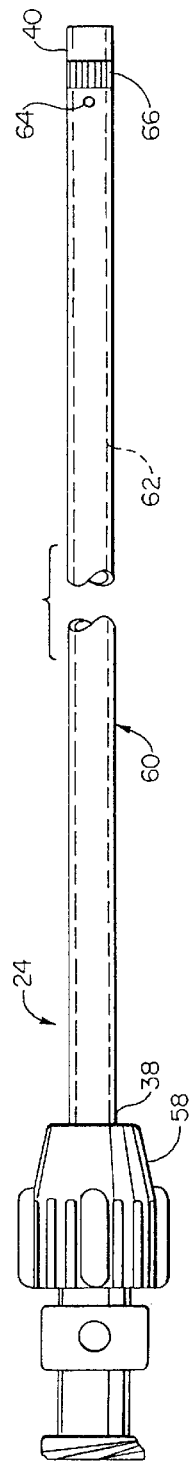
FIG. 3 is an enlarged side view of a push catheter portion of the delivery system in accordance with the present invention.

The push catheter 24 is shown in greater detail in FIG. 3. The push catheter 24 includes a female luer lock connector 58 and a push catheter body 60. The push catheter body 60 is defined by the proximal end 38 and the distal end 40, and includes a central lumen 62, an opening 64 and a radiopaque marking 66.

The female luer lock connector 58 is of a type commonly known in the art and is attached to the proximal end 38 of the push catheter body 60. In a preferred embodiment, the female luer lock connector 58 includes a transverse opening (not shown) in communication with the central lumen 62.

The central lumen 62 of the push catheter body 60 extends from the proximal end 38 to the distal end 40. As described in greater detail below, the central lumen 62 has a diameter greater than an outer diameter of the guide catheter body 48 (FIG. 2). The opening 64 is positioned near the distal end 40 of the push catheter body 60, passing from an outer circumference of the push catheter body 60 to the central lumen 62. Finally, the radiopaque marking 66 is positioned near the distal end 40 of the push catheter body 60 to facilitate fluoroscopic positioning of the push catheter 24.

The push catheter body 60 is preferably formed of a relatively rigid biocompatible polymer through an extrusion process. Alternatively, a biocompatible metal may be used. The push catheter body 60 has a length less than the length of the guide catheter body 48. Following extrusion of the push catheter body 60, the female luer lock connector 58 is attached to the proximal end 38.

Figure 4:
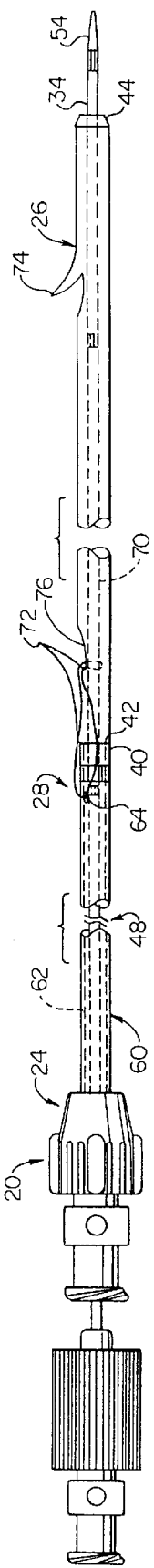
FIG. 4 is a side view of the assembled delivery system in accordance with the present invention.

The stent 26, in conjunction with the delivery system 20, is shown in greater detail in FIG. 4. The stent 26 includes the proximal end 42, the distal end 44, a central lumen 70, a proximal barb 72 and a distal barb 74. The central lumen 70 extends from the proximal end 42 to the distal end 44. The proximal barb 72 extends outwardly in a distal fashion from an outer circumference of the stent 26. In a preferred embodiment, the proximal barb 72 creates a passage 76 (shown partially in FIG. 4) extending from an outer circumference of the stent 26 to the central lumen 70. Similarly, the distal barb 74 extends from an outer circumference of the stent 26 in a proximal fashion. The proximal barb 72 and the distal barb 74 assist in maintaining position of the stent 26 within a body cavity. The barbs are opposed to one another to prevent stent migration in either axial direction.

The central lumen 70 of the stent 26 is sized to slidably engage the guide catheter 22. In this regard, the central lumen 70 has a diameter greater than an outer diameter of the guide catheter body 48. Further, the stent 26 has a length less than a length of the guide catheter body 48. Thus, upon final assembly, the push catheter 24 and the stent 26 have a combined length less than that of the guide catheter body 48.

The stent 26 is preferably formed from a biocompatible, relatively flexible material, such as plastic. Alternatively, a biocompatible metal may be used. In one preferred embodiment, the stent 26 is coated with a hydrophilic lubricant on the outer circumference to facilitate movement of the stent 26 within a body cavity. Additionally, the lubricious coating assists in reducing the potential for encrustation within the body cavity. In this regard, the central lumen 70 may also be coated with a hydrophilic material to facilitate movement of the stent 26 along the guide catheter body 48, as well as limit encrustation of the stent 26. Finally, the proximal barb 72 and the distal barb 74 are preferably formed in the stent 26 by imparting properly positioned cuts through the stent wall. Other agents, such as antimicrobial agents, may be incorporated into the stent coating or polymer.

While the delivery system 20 of the present invention has been described as preferably including the stent 26, other components may be used. More particularly, the stent 26 may be a drainage catheter or similar device. Similar to the stent 26 shown in FIG. 4, the drainage catheter (not shown) includes a central lumen sized to slidably engage an outer circumference of the guide catheter body 48. Further, the drainage catheter is preferably configured to include a passage similar to the passage 76 of the stent 26 shown in FIG. 4 for receiving the retention device 28. Thus, for purposes of this description, the term "stent" is interchangeable with the term "drainage catheter", as will be understood by one skilled in the art.

As shown in FIG. 4, the retention device 28 is preferably a flexible thread. In one preferred embodiment, the retention device 28 is a biocompatible suture. The suture can be a thread, filament or wire. Alternatively, the retention device 28 can be a biocompatible wire or cable. Regardless, the suture 28 preferably extends from the distal end 40 of the push catheter 24. As described in greater detail below, the suture 26 connects the push catheter 24 to the stent 26 via the opening 64 in the push catheter 24 and the passage 76 in the stent 26.

As shown in FIG. 4, the delivery system 20 is assembled prior to insertion into the body either by the manufacturer or by the physician by sliding the push catheter 24 over the guide catheter body 48. As previously described, the push catheter 24 includes a central lumen 62 having a diameter greater than that of the guide catheter body 48. The proximal end 38 of the push catheter 24 is maneuvered toward the proximal end 30 of the guide catheter body 48 until the distal end 34 of the guide catheter body 48 extends slightly from the distal end 40 of the push catheter 24. The proximal end 42 of the stent 26 is then positioned about the distal end 34 of the guide catheter body 48. The retention device 28 is used to secure the push catheter 24 to the stent 26.

More particularly, as shown in FIG. 5, the distal end 40 of the push catheter body 60 includes the opening 64. As previously described, the opening 64 passes from the central lumen 62 to an outer circumference of the push catheter body 60.

As shown in FIG. 6, the retention device 28, which in the preferred embodiment is a flexible thread or suture, is threaded through the opening 64 in the push catheter body 60. In this regard, the suture 28 includes a first end 80 and a second end 82. The suture 28 is positioned through the opening 64 such that the first end 80 extends away from an outer circumference of the push catheter body 60. Conversely, the second end 82 of the suture 28 extends within the central lumen 62 of the push catheter body 60.

As shown in FIG. 7, the guide catheter body 48 is slidably directed within the central lumen 62 of the push catheter body 60 until the distal end 40 of the push catheter body 60 is proximal the distal end 34 of the guide catheter body 48. The stent 26 is axially placed over the guide catheter body 48. As shown in FIG. 7, when the stent 26 is first placed over the guide catheter body 48, the distal end 34 of the guide catheter body 48 is initially directed through the central lumen 70 of the stent 26 at the proximal end 42. Subsequently, the distal end 34 of the guide catheter body 48 is directed outwardly from the central lumen 70 of the stent 26 via the passage 76 created by the proximal barb 72. Once so positioned, the stent 26 is slid over the guide catheter body 48 to a position in close proximity to the distal end 34 of the push catheter body 60. Notably, the second end 82 of the suture 28 is maneuvered away from the central lumen 62 of the push catheter body 60, above an outer circumference of the stent 26.

As shown in FIG. 8, the second end 82 of the suture 28 is looped around the guide catheter body 48, distal the proximal barb 72 of the stent 26. Thus, in the position shown in FIG. 8, the suture 28 forms a loop 84 about the guide catheter body 48. The loop 84 is maneuvered toward the proximal barb 72 of the stent 26 by pulling the second end 82 of the suture 28 toward the distal end 40 of the push catheter body 60. With the loop 84 positioned near the proximal barb 72 of the stent 26, the guide catheter body 48 is retracted relative to the stent 26. More particularly, the distal end 34 of the guide catheter body 48 is slowly directed into the passage 76 of the stent 26. During this retraction movement, the loop 84 of the suture 28 remains engaged with the guide catheter body 48. Once the tapered tip 54 of the guide catheter body 48 clears the passage 76 of the stent 26, the distal end 34 of the guide catheter body 48 is re-inserted into the central lumen 70 of the stent 26.

As shown in FIG. 9, the distal end 34 of the guide catheter body 48 is now entirely within the central lumen 70 of the stent 26. Further, the loop 84 of the suture 28 passes through the passage 76 of the stent 26 and remains engaged with the guide catheter body 48. The distal end 34 of the guide catheter body 48 is then slid forward relative to the stent 26 so that the loop 84 of the suture 28 remains in contact with the guide catheter body 48. It is recognized that in an alternative embodiment, a separate hole could be made in the stent wall for passing the suture through, rather than using the passage 76 that is created by forming the barb.

Figure 10:
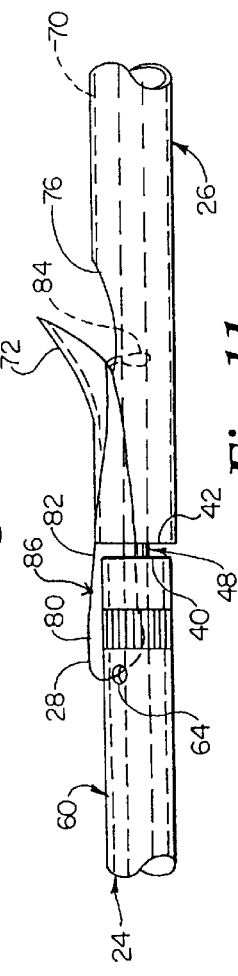

Finally, as shown in FIG. 10, the first end 80 and the second end 82 of the suture 28 are secured to one another, forming a knot 86. Thus, upon final assembly, the suture or retention device 28 connects the push catheter 24 to the stent 26 so long as the loop 84 is engaged with the guide catheter body 48.

During use, the delivery system 20 is pre-assembled as previously described. In a preferred embodiment, an endoscope is positioned within a body cavity so that a distal end of the endoscope is located near a stricture to be stented or other desired location.

The distal end 34 of the guide catheter 22 preferably extends outwardly from the distal end 44 of the stent 26 (shown in FIG. 4). As previously described, the distal end 34 of the guide catheter 22 includes the tapered tip 54. As the guide catheter body 48 exits the distal end of the endoscope, the tapered tip 54 dilates the stricture. It is recognized that this placement can be accomplished over a guide wire which has been previously placed across a stricture with the guide catheter including a lumen which threads over the guide wire.

Once the distal end 34 of the guide catheter body 48 is properly positioned, the stent 26 is then positioned within the body cavity. More particularly, the guide catheter 22 is held in a stationary position. The push catheter 24 is then moved forward (to the right in FIG. 10) such that the distal end 40 of the push catheter 24 contacts the proximal end 42 of the stent 26. Continued forward movement of the push catheter 24 imparts a similar movement onto the stent 26. If retraction (leftward movement with reference to FIG. 10) of the stent 26 is required, the guide catheter body 48 is again held stationary. The push catheter 24, in turn, is retracted. Retraction of the push catheter 24 creates a leftward movement on the suture 28 via the opening 64. Because the suture 28 is secured to the guide catheter 22 via the loop 84, retraction of the push catheter 24 will cause the suture 28 to become relatively taut. At this point, the suture 28 imparts a leftward or retraction movement onto the stent 26 via contact between the suture and the stent 26 at the passage 76. Notably, the loop 84 will slide along the guide catheter body 48 such that once the suture 28 is taut, retraction of the push catheter 24 results in retraction of the stent 26.

Figure 11:
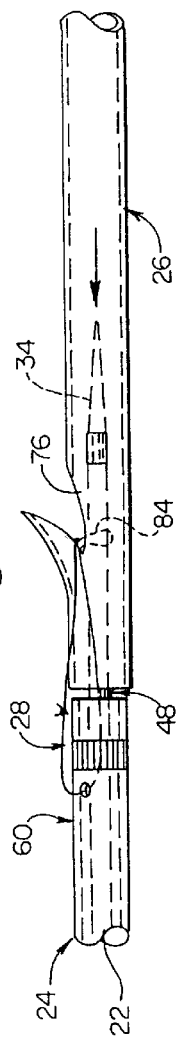
FIGS. 11–13 illustrate use of the delivery system of the present invention, including release of the retention device.

Once the stent 26 is positioned within the body cavity at a desired location, the guide catheter 22, the push catheter 24 and the retention device or suture 28 are removed. More particularly, as shown in FIG. 11, the suture 28 is disengaged from the stent 26 by first retracting the guide catheter body 48 while the push catheter 24 is held stationary. As previously described, the loop 84 slides along the guide catheter body 48. Retraction of the guide catheter 22 continues until the distal end 34 clears the loop 84. In other words, the loop 84 continues to slide along the guide catheter body 48 as the guide catheter 22 is retracted. Once the distal end 34 of the guide catheter body 48 is approximately equal with the passage 76 in the stent 26, the loop 84 will slide off of, or out of engagement with, the guide catheter body 48.

Figure 12:
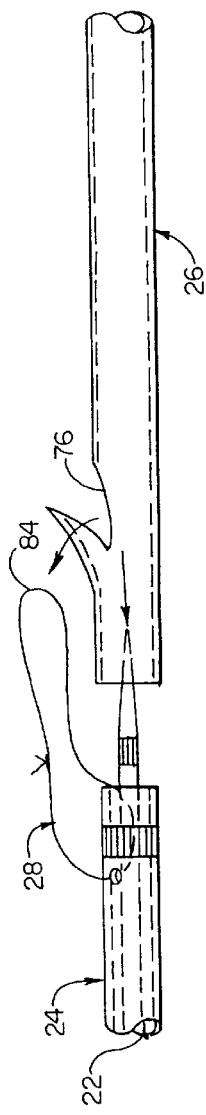
Figure 13:
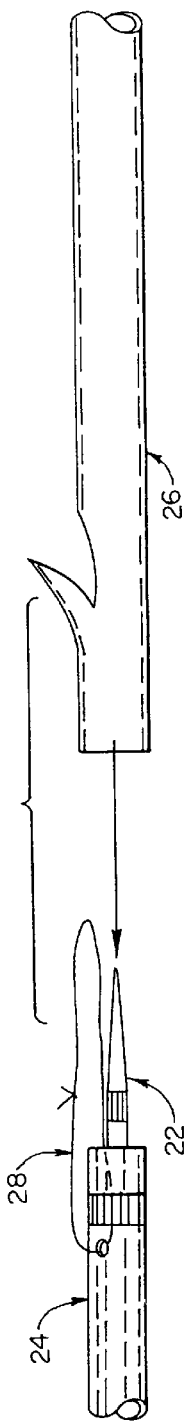

As shown in FIG. 12, once the loop 84 is free from the guide catheter body 48, the guide catheter 22 and the push catheter 24 can be retracted from the body cavity. Retraction (or leftward movement in FIG. 12) of the push catheter 24 pulls the suture 28 out of the passage 76 and away from the stent 26. Finally, as shown in FIG. 13, the guide catheter 22, the push catheter 24 and the suture 28 are completely removed from the body cavity, leaving the stent 26 permanently positioned within the body cavity.

The delivery system of the present invention presents a unique, single-step approach for delivering a drainage catheter or stent drainage catheter. Unlike prior procedures which require numerous components and time-consuming steps for correcting minor misplacement of the drainage catheter or stent, the delivery system of the prevent invention is a single, pre-assembled tool which provides for both forward and rearward movement of the drainage catheter or stent within the body cavity. Further, in one preferred embodiment, incorporation of various radiopaque markings in conjunction with lubricious coating on the drainage catheter or stent facilitates proper device placement.

In another alternative embodiment, the suture 28 could be permanently attached to the stent and temporarily to the push catheter through a loop extending through a hole in the push catheter. Essentially the ends of the suture would be reversed from the previous embodiments. The suture could be used to facilitate stent removal if left in place on the stent.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims. For example, while the retention device has been preferably described as being a suture threaded through a hole created in the push catheter, other retention devices are equally acceptable. In this regard, the retention device can be a flexible thread permanently attached to the push catheter. Alternatively, the retention device can be an interlocking device positioned at the distal end of the push catheter, configured to be releasably attached to the proximal end of the drainage catheter or stent. With this configuration, the push catheter can engage and disengage the drainage catheter or stent by simple rotational movement of the push catheter relative to the drainage catheter or stent.

The preferred embodiment has described the use of radiopaque markings on both the guide catheter and the push catheter. It should be understood, however, that the radiopaque markings are not required elements. Alternatively, radiopaque markings may be included on the drainage catheter or stent.

Similarly, the preferred embodiment includes a lubricious coating on both the distal end of the guide catheter and the drainage catheter or stent. This coating is not a requirement. In this regard, the guide catheter and drainage catheter or stent may be manufactured to form a smooth surface. Further, the entire guide catheter body may be coated with a lubricant to facilitate sliding of the push catheter and the drainage catheter or stent along the guide catheter body.

What is claimed is:

1. A drainage stent delivery system, comprising:

a guide member;

a placement catheter having a distal portion and being disposed on the guide member;

a drainage stent having a proximal portion and being disposed on the guide member distal of the placement catheter; and a means for releasably connecting the distal portion of the placement catheter to the proximal portion of the stent, wherein the releasable connecting means is connected to the distal portion of the placement catheter, said connecting means releasing said drainage stent upon displacement of the guide member.

2. A delivery system as in claim 1, wherein the releasable connecting means comprises a tying mechanism.

3. A delivery system as in claim 2, wherein the tying mechanism comprises a flexible thread.

4. A delivery system as in claim 3, wherein the drainage stent has a proximal passage near a proximal end of the drainage stent, wherein the flexible thread passes through the proximal passage in the stent.

5. A delivery system as in claim 4, wherein the placement catheter has a distal passage near a distal end of the placement catheter, wherein the flexible thread passes through the distal passage in the placement catheter.

6. A delivery system as in claim 5, wherein the flexible thread forms a loop around the guide member disposed in the stent.

7. A delivery system as in claim 6, wherein the loop passes through the passage in the stent.

8. A delivery system as in claim 1, wherein the displacement is longitudinal.

9. A delivery system as in claim 8, wherein the displacement is in a proximal direction.

* * * * *